US012674191B1

(12) United States Patent
Gibbs-Davis et al.

(10) Patent No.: US 12,674,191 B1
(45) Date of Patent: Jul. 7, 2026

(54) METHOD OF LIGATION FOR THE DETECTION OF ABASIC SITES ON A DNA TARGET SEQUENCE

(71) Applicants: Julianne M. Gibbs-Davis, Edmonton/Alberta (CA); Hansol Park, Totonto (CA)

(72) Inventors: Julianne M. Gibbs-Davis, Edmonton/Alberta (CA); Hansol Park, Totonto (CA)

( * ) Notice: Subject to any disclaimer, the term of this patent is extended or adjusted under 35 U.S.C. 154(b) by 490 days.

(21) Appl. No.: 18/208,758

(22) Filed: Jun. 12, 2023

Related U.S. Application Data

(60) Provisional application No. 63/351,333, filed on Jun. 10, 2022.

(51) Int. Cl.
$$C12Q\ 1/6827\quad(2018.01)$$
$$C12Q\ 1/6862\quad(2018.01)$$

(52) U.S. Cl.
CPC ......... C12Q 1/6827 (2013.01); C12Q 1/6862 (2013.01); *C12Q 2600/166* (2013.01)

(58) Field of Classification Search
CPC ............... C12Q 1/6827; C12Q 1/6862; C12Q 2600/166
See application file for complete search history.

(56) References Cited

U.S. PATENT DOCUMENTS 9,193,993 B1 * 11/2015 Gibbs-Davis ........ C12Q 1/6853
2018/0127830 A1 * 5/2018 Gerson ................ C12Q 1/6827

OTHER PUBLICATIONS

Matray and Kool, Selective and Stable DNA Base Pairing without Hydrogen Bonds, 1998, J Am Chem Soc., 120(24), 6191-6192 (Year: 1998).*
Østergaard and Hrdlicka, Pyrene-functionalized oligonucleotides and locked nucleic acids (LNAs): Tools for fundamental research, diagnostics, and nanotechnology, 2011, Chem Soc Rev, 40, 5771-5788 (Year: 2011).*
Osman et al., Enhanced mismatch selectivity of T4 DNA ligase far above the probe: Target duplex dissociation temperature, 2021, Biopolymers, 112, e23393 (Year: 2021).*

* cited by examiner

*Primary Examiner* — Samuel C Woolwine
*Assistant Examiner* — Kara N Kovach
(74) *Attorney, Agent, or Firm* — Invention To Patent Services; Alex Hobson

(57) ABSTRACT

A method of ligating a ligation product for detecting abasic sites on DNA target sequence is described. The ligation method uses a pyrene probe that ligates with a second probe in the presence of a ligase. A pyrene may comprise 5'-phosphate 1'-pyrene deoxyribonucleotide at the 5'-terminus. The second probe may comprise a terminal 3'-hydroxy, wherein the 3'-hydroxy is ligated with the pyrene probe. The ligase may be T4 DNA Ligase or PBCV-1 as the latter has been found to improve selectivity. The abasic on the DNA target sequence may be naturally occurring or may be a generated abasic that is formed by the addition of an enzyme. Furthermore, selectivity may be increase by the addition of adenosine triphosphate (ATP) or ligating at a temperature above the probe:target sequence thermal disassociation temperature.

19 Claims, 5 Drawing Sheets

METHOD OF LIGATION FOR THE DETECTION OF ABASIC SITES ON A DNA TARGET SEQUENCE

CROSS REFERENCE TO RELATED APPLICATIONS

This application claims the benefit of priority to U.S. provisional patent application No. 63/351,333, filed on Jun. 10, 2022; the entirety of which is incorporated by reference herein.

BACKGROUND OF THE INVENTION

The invention relates to a method of ligating to form a ligation product for detecting abasic sites on a DNA target sequence using a pyrene probe that ligates with a second probe in the presence of a ligase.

BACKGROUND

DNA damage occurs continuously as a consequence of exposure to genotoxic agents and endogenous processes. The most common lesion observed in DNA is an apurinic or apyrimidinic site called the abasic site, which is estimated to occur ~10,000 times in a human cell per day. Although most of this damage is repaired by the DNA repair system, remaining or undetected abasic sites can cause mutations or trigger acute toxicities in cells when accumulated. Owing to the broad role of abasic sites in biology, it is important to detect their presence and location and also understand their formation within genomic DNA. The most common method to detect abasic sites employs aldehyde-reactive probes (ARPs) that react with the open form of the deoxyribose of the abasic site. However, the main shortcoming of this method is the cross-reactivity caused by other reactive aldehydes in DNA that do not arise from abasic sites. Recently, strategies to detect abasic sites with single-nucleotide resolution were reported which add chemical steps to enhance the specificity of ARP-based methods.

SUMMARY OF THE INVENTION

The invention is directed to a method of ligating a ligation product for detecting abasic sites on a DNA target sequence using a pyrene probe that ligates with a second probe in the presence of a ligase. A pyrene probe is a probe having a pyrene such as probe comprising 5'-phosphate 1'-pyrene deoxyribonucleotide at the 5'-terminus. The pyrene probe could consist of a pyrene at the 1'-position or could be a compound that includes pyrene at the 1'-position of the deoxyribonucleotide. The second probe that is ligated with the pyrene probe may be a 3'-hydroxy probe having a terminal 3'-hydroxy, wherein the 3'-hydroxy is ligated with the pyrene probe. The ligase may be T4 DNA ligase or PBCV-1 DNA Ligase, a *Chlorella* virus DNA Ligase, as the latter has been found to improve selectivity. The abasic on the DNA target sequence may be naturally occurring or may be a generated abasic that is formed by the addition of an enzyme. The generated abasic sites may be formed by the addition of the enzyme before ligating the pyrene probe with the second probe in the presence of a ligase. Furthermore, selectivity of the ligation reaction such that it only occurs in proximity to an abasic site on the target may be increased by varying the concentration of adenosine triphosphate (ATP). The ATP may be added at the standard concentration of 1 millimolar or in an elevated concentration of more than 1 millimolar, 5 millimolar or more, 10 millimolar or more, 15 millimolar or more, 20 millimolar or more and any range between and including the concentrations provided. An improved selectivity was found at 15 millimolar as reported herein. Also, improved selectivity such that ligation only occurs in the presence of the abasic site may be achieve when the ligation is performed at elevated temperatures above the probe:target sequence thermal disassociation temperature, the lowest temperature where 50% of the probe: target duplex is disassociated in the absence of the ligase. The elevated temperature may be 5° C. or more, 10° C. or more, 20° C. or more, 30° C. or more from the probe:target sequence thermal disassociation temperature.

Remarkable selectivity was observed in the ligation of 5'-phosphate 1'-1-pyrene deoxyribonucleotide terminated strands across from an abasic lesion in a DNA-templated ligation reaction by two different ligases suggesting that pyrene-terminated strands could be used in abasic site detection. Specifically, by increasing the ATP concentration with T4 DNA ligase as the ligase or using standard 1 mM concentrations of ATP with PBCV-1 DNA ligase efficient ligation of the pyrene probe was observed when it was across from the abasic but not other canonical nucleobases. This selectivity of the pyrene:abasic pairing was much greater than the selectivity observed in the canonical T:A basepair.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1A:
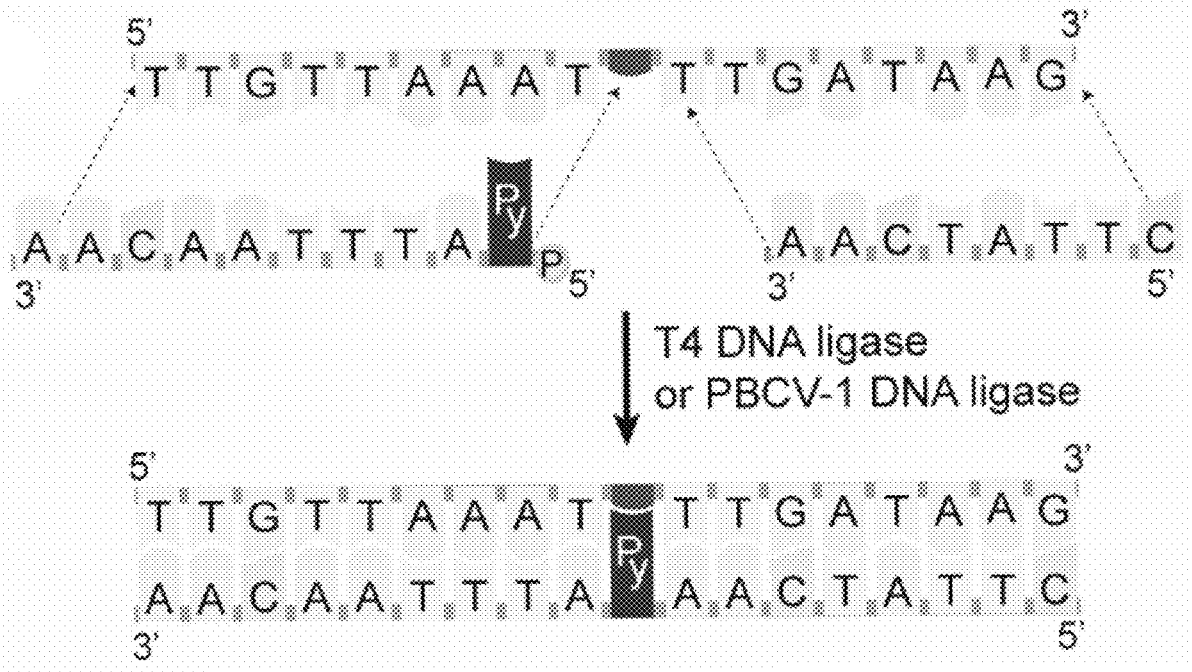
FIG. 1A and FIG. 1B show schematic diagrams of selective ligation of the pyrene strand on the abasic site.

Corresponding reference characters indicate corresponding parts throughout the several views of the figures. The figures represent an illustration of some of the embodiments of the present invention and are not to be construed as limiting the scope of the invention in any manner. Some of the figures may not show all of the features and components of the invention for ease of illustration, but it is to be understood that where possible, features and components from one figure may be included in the other figures. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Figure 1B:
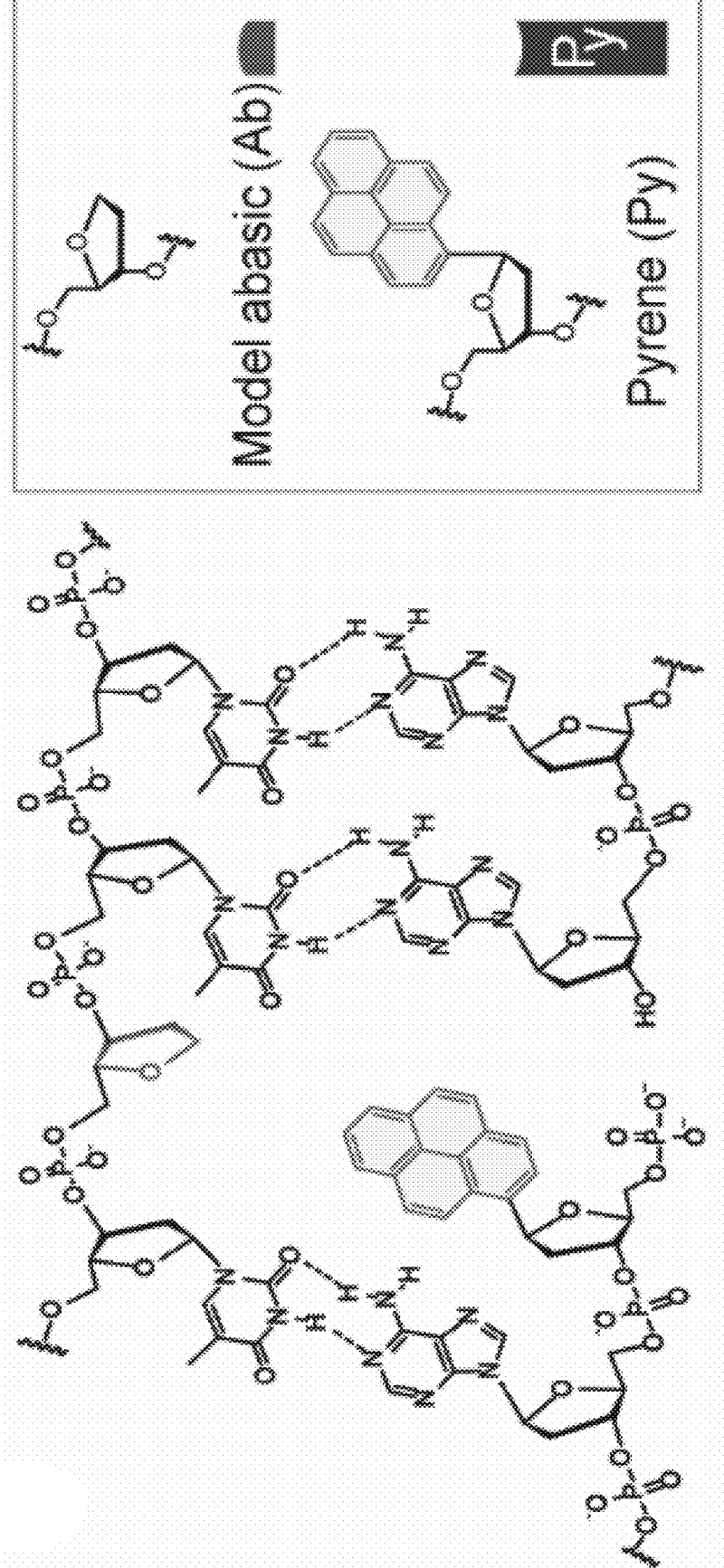

Herein the highly selective and efficient enzymatic ligation of 5'-phosphate pyrene nucleotide-terminated strands across from an abasic group in the template strand is reported (FIG. 1). FIG. 1 shows a schematic diagram of a selective ligation of the pyrene probe strand on the abasic site, wherein (A) shows successful ligation of pyrene strand across from the abasic site, and (B) shows the molecular structure depicting the pyrene:abasic base pair in a duplex. To optimize selectivity, the ligase, ATP concentration and temperature were varied. A competition assay was also utilized, which led to selective recognition of an abasic-containing template in the presence of thymine-containing template. The elective ligation of pyrene-terminated strands could be used in a strategy for detecting abasic lesions at specific sites as a biomarker of disease or disease progression.

Figure 2A:
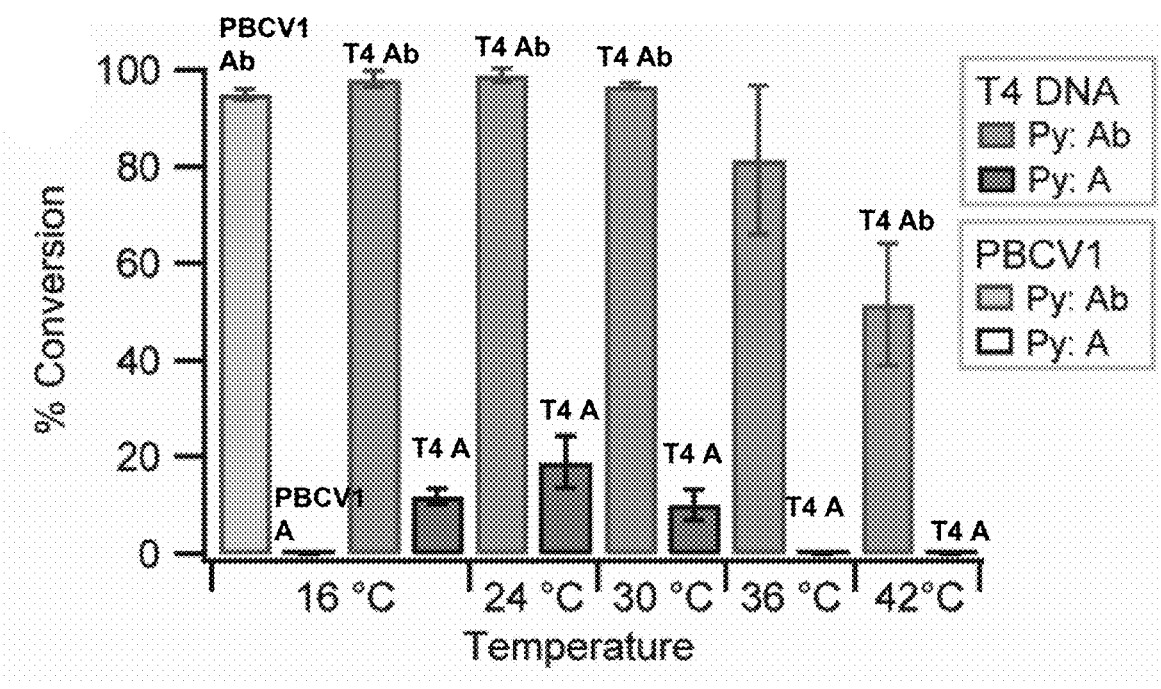
FIG. 2A and FIG. 2B show graphs of results of T4 DNA ligase catalyzed ligation of the 5'-phosphate pyrene strand using an abasic or adenine template.
Figure 2B:
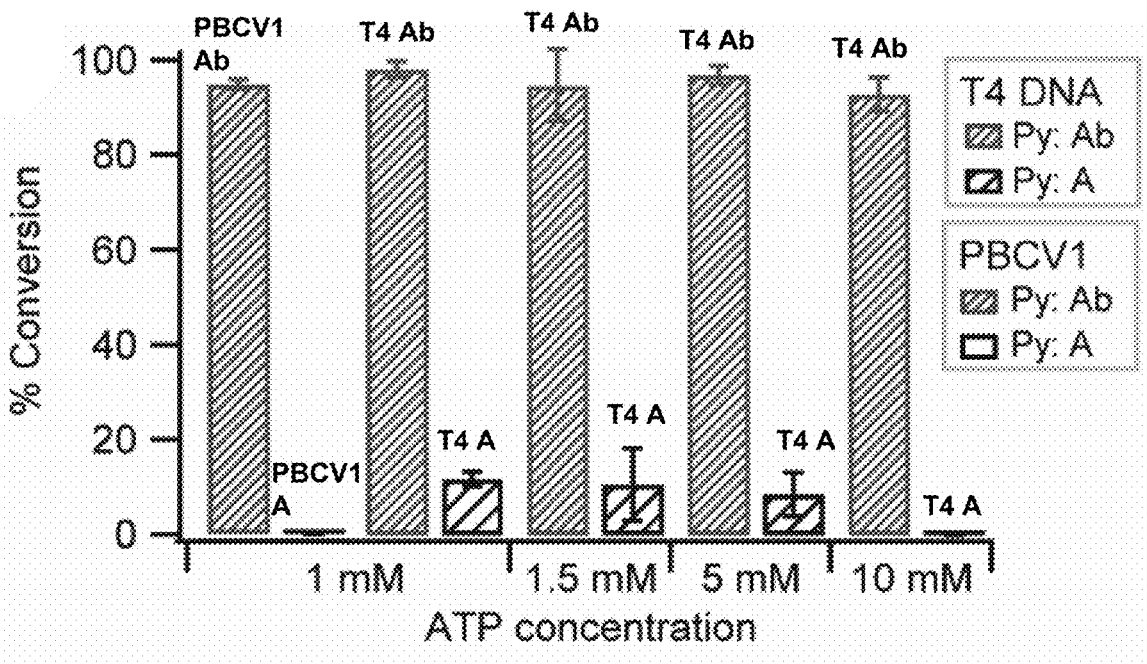

In previous work, the enzymatic ligation of unnatural nucleotides used T4 DNA ligase, which is the most widely used ligase in molecular biology. With the exception of model 1'-H-abasic groups, these ligation studies had been limited to nucleobases containing heteroatoms. To see whether the T4 DNA ligase tolerated the bulky pyrene substituent at the 5'-position of the ligation site, the ligation of a fluorescein-labeled 3'-OH terminated strand and a 5'-phosphate pyrene strand in the presence of a DNA template containing either the abasic group or an adenine across from the pyrene was monitored. Using polyacrylamide gel electrophoresis with fluorescent imaging, the ligation % yield versus time was determined based on the presence of the new ligation product band. The ligation using another ATP-dependent ligase, chlorella virus PBCV-1 DNA ligase was also monitored. Recent studies comparing the two ligases' catalytic efficiencies for DNA substrates with different blunt-end and overhang architectures revealed different selectivities. Therefore, their efficiencies at ligating an unnatural pyrene nucleotide were compared. Unexpectedly, both DNA ligases allowed for rapid ligation of the 5'-phosphate pyrene strand when positioned across from an abasic group on the template (FIG. 2A and FIG. 2B). For example, under standard conditions the 5'-phosphate pyrene strand was ligated across from the abasic template as rapidly as a 5'-phosphate thymine across from the complementary A template (FIG. 1A). However, T4 DNA ligase still facilitated the ligation of the pyrene strand when positioned across from an A on the template (10% yield after 60 min). In contrast, the PBCV-1 DNA ligase did not show any activity for the pyrene:A base pair.

FIG. 2 shows T4 DNA ligase catalyzed ligation of the 5'-phosphate pyrene strand using an abasic or adenine template. The ligation was evaluated after 10 minutes and analyzed by PAGE gel. FIG. 2A shows the temperature variation with 1 mM ATP FIG. 2B shows ATP variation at 16° C. Experimental conditions: 2.8 µM of the 5'-phosphate pyrene strand, 1.4 µM of the fluorescein-labeled strand, and 1.4 µM of the template strands. T4 DNA ligase (400,000 CEU/mL, 1 µL per 15 µL total volume) in 50 mM Tris-HCl, 10 mM MgCl2 and 1 mM ATP concentrations.

Next, varying the conditions of ligation was explored with T4 DNA ligase to see whether the ligation of the 5'-phosphate pyrene strand across from A could be suppressed. First, the temperature was varied from 16° C. to 42° C. in the ligation reaction (FIG. 2A) as our previous work had found that the discrimination of T4 DNA ligase against mismatched base pairs was greatly increased at higher temperatures well above the melting temperature (TM) of the nicked DNA duplex.30 The difference in ligation yield between the abasic template and the adenine template was distinct for all temperatures, especially at the higher temperatures (36° C. and above) where the ligation with the adenine-containing template did not occur (FIG. 2A). This result agreed with our previous observations that the elevated temperature above the TM increased the selectivity of ligation for the matched base pair, in this case, the stable pyrene:abasic pair. Overall, T4 DNA ligase and PBCV-1 DNA ligase successfully catalysed the ligation of the bulky pyrene at the 5'-position of the nick when the abasic template was used.

To further optimize the conditions for T4 DNA ligase, which was less intrinsically discriminating compared with PBCV-1 DNA ligase, the effect of ATP concentration on the ligation reaction was explored since ATP is a cofactor of T4 DNA ligase and previous studies have shown that the concentration of ATP affects the ligation rate and fidelity of the enzyme. For ligation reactions where the substrates are slower owing, for example, to mismatches at the ligation site, the ligase can dissociate from the adenylated DNA complex and become quickly readenylated making it unable to catalyse the ligation leading thereby reducing ligation efficiency.34 The ligation reactions were performed at 16° C. with different ATP concentrations above the standard concentration of ATP (1 mM), which should make the readenylation of the enzyme even faster. At 1.5 and 5 mM ATP, the T4 DNA ligase ligated not only the pyrene:abasic pair efficiently (~100%) but also the unfavoured pyrene:A pair to varying amounts (FIG. 2B). However, at 10 mM ATP, ligation was only observed with the pyrene:abasic pair without compensating the % yield. This unexpected and surprising increase in selectivity at elevated ATP concentration indicated that the enzyme could more rapidly ligate the pyrene strand across from the abasic rather than across from the dA nucleotide. The selectivity of the pyrene-containing template for ligation of 5'-phosphate abasic versus 5'-phosphate adenine strands was also explored. Interestingly, very little selectivity with T4 DNA ligase (FIG. 2B) was observed. In contrast, PBCV-1 DNA ligase was quite selective for the ligation 5'-phosphate abasic strand when paired across from the pyrene-containing template.

The ATP and temperature variation studies indicated that the selective ligation of the pyrene strand could be tuned significantly by the reaction conditions, opening up its possible use in the detection of abasic lesions. To utilize the ligation of a probe or primer bearing a 5'-phosphate pyrene probe as a method of detecting abasic lesions, the selectivity across from all of the canonical bases must be evaluated. Accordingly, five different templates containing the natural bases (A, T, G, and C) or the abasic lesion were tested in the ligation of the 5'-phosphate pyrene terminated strand (FIG. 3).

Figure 3A:
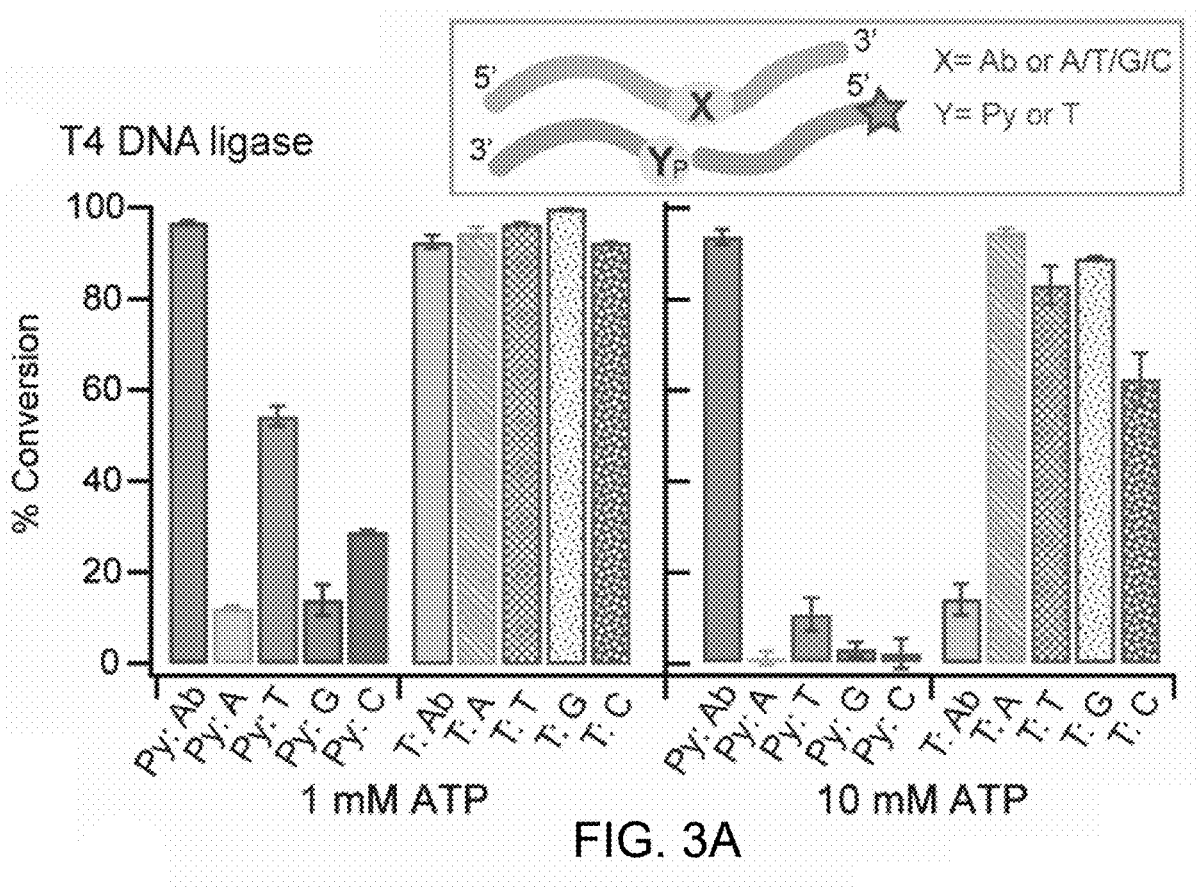
FIG. 3A show a graph of a results of a selectivity with 5'-phosphate pyrene strand with 5'-phosphate thymine strand with various templates.
Figure 3B:
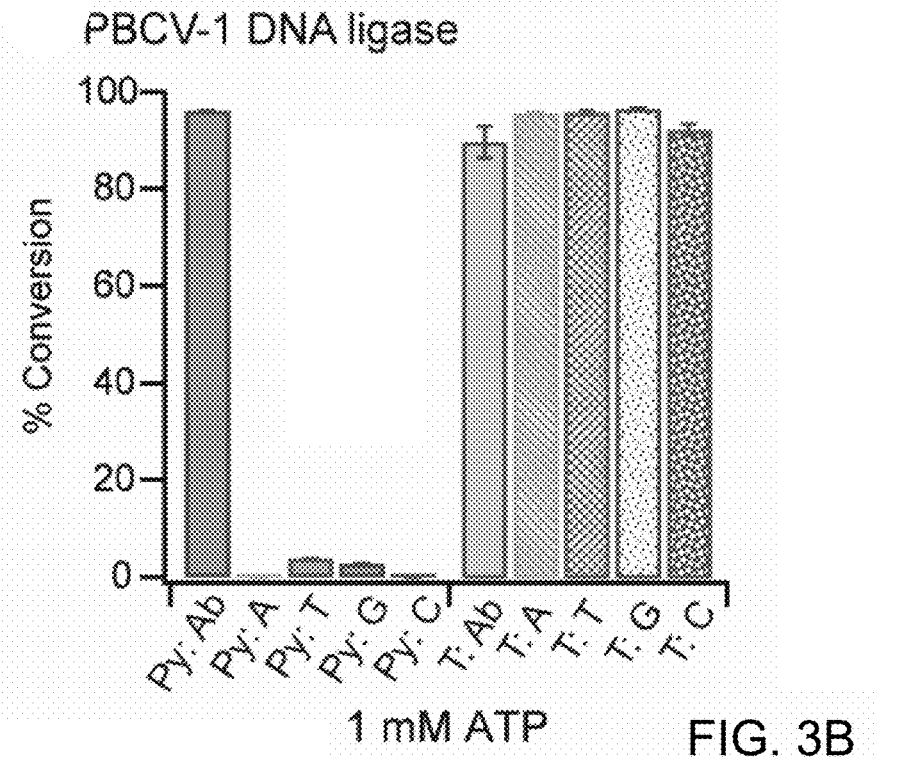
FIG. 3B show a graph of a results of a selectivity with 5'-phosphate pyrene strand with 5'-phosphate thymine strand with various templates.

FIG. 3 shows the selectivity comparison with 5'-phosphate pyrene strand with 5'-phosphate thymine strand with various templates. FIG. 3A shows T4 DNA ligase. FIG. 3B shows PBCV-1 DNA ligase. Experimental conditions:2.8 μM of the 5'-phosphate strand, 1.4 μM of the fluorescein-labeledstrand, and 1.4 μM of the template strands.T4 DNA ligase (400,000 CEU/mL, 1 μL per 15 μL total volume) or PBCV-1 DNA ligase (25,000 units/mL, 1.5 μL per 15 μL total volume) in 50 mM Tris-HCl, 10 mM MgCl2 and variousATP concentrations at 16° C. Data were evaluated in 10 minutes.

With T4 DNA ligase at 16° C. and varying ATP concentrations, minor amounts of ligation were observed with thymine template (~10%) and guanine template (<5%) in 10 mM ATP (FIG. 3A). However, the pyrene nucleotide exhibited ligation in the presence of only the abasic template when the ATP concentration was increased to 15 mM albeit with somewhat reduced yields. Upon increasing the ligation temperature to 36° C. with 1 mM ATP, the ligation selectivity somewhat improved compared with 16° C. but increasing the ATP concentration to 10 mM at 36° C. dramatically reduced the yield. As a point of comparison, similar ligation experiments were performed using T(thymidine) in place of the pyrene, revealing very little discrimination under the same experimental conditions, which is consistent with previous studies of T4 DNA ligase tolerance for mismatches at the 5'-position of the nick. These results reveal that the 5'-phosphate pyrene is uncommonly discriminating at this position compared with a canonical 5'-phosphate thymidine terminated strand. Finally, using PBCV-1 DNA ligase under standard conditions (1 mM ATP, and 16° C.) led to efficient ligation of the 5'-phosphate pyrene only with the abasic template consistent with our earlier observations (FIG. 3B). However, similar to T4 DNA ligase, this enhanced discrimination was not observed for ligation of the 5'-phosphate thymidine terminated strand, which was facilely ligated across from all of the canonical nucleobases as well as an abasic-containing template.

To further investigate the selectivity of the ligation of the 5'-phosphate pyrene nucleotide for the template containing the "complementary" abasic group (Template(Ab)), a competitive ligation reaction was performed at 16° C. using 5'-phosphate strands containing either the terminal pyrene nucleotide (Probe(Py)) or a thymidine nucleotide (Probe (T)). The 5'-phosphate thymine strand (Probe(T)) which was complementary to an adenine-containing template (Template(A)) was prepared with an extra three nucleotides. As such, when both 5'-phosphate modified probes (Probe(T) or Probe(Py)) were present, their ligated products were distinguishable based on the ligated product length (18 nucleotides (nt) for the pyrene strand vs 21 nt for the thymine strand). Each lane contained a different combination of DNA probes and templates to see whether the selectivity of pyrene nucleotides could be achieved in a mixture of DNA sub-

Figure 4:
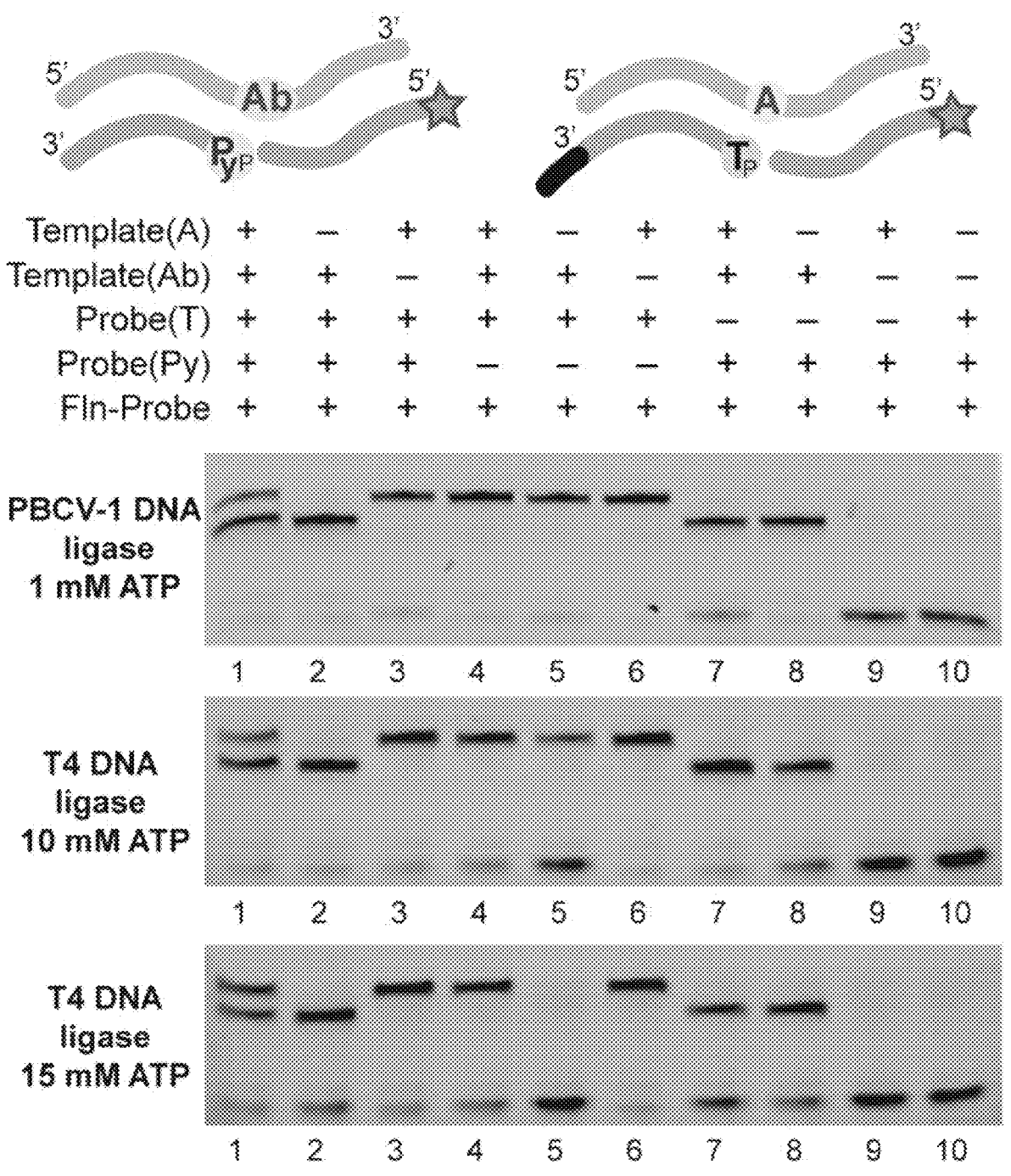
FIG. 4 shows results of a ligation competition experiment.

6 strates (FIG. 4). Two different ATP concentrations (10 mM and 15 mM) were tested with T4 DNA ligase, while the standard ATP concentration (1 mM) for PBCV-1 DNA ligase was used.

FIG. 4 shows a ligation competition experiment. The reaction was evaluated after 10 min at 16° C. Experimental conditions: 2.8 μM of the 5'-phosphate strand, 1.4 μM of the fluorescein-labeled strand, and 0.7 μM or 1.4 μM of the template strands. The sum of the templates added was consistent as 1.4 μM, T4 DNA ligase (400,000 CEU/mL, 1 μL per 15 μL total volume) or PBCV-1 DNA ligase (25,000 units/mL, 1.5 μL per 15 μL total volume) in 50 mM Tris-HCl, 10 mM MgCl2. ATP concentration was indicated in the figure.

In the presence of both templates and both probe strands, similar amounts of each ligated product were observed suggesting selective ligation of each probe based on hybridization with its corresponding template. In the presence of both 5'-phosphate strands but only one template, the ligated product was completely determined based on the template that was present, illustrating that ligation was very selective under competitive conditions (lanes 2 and 3). However, in the absence of competition, the fidelity of the thymine terminated strand was poor exhibiting ligation in the presence of the abasic template except when 15 mM ATP and T4 DNA ligase were used where excellent selectivity was observed (lane 5). As expected based on our observations described in [0022], the fidelity of the pyrene terminated strand was excellent even in the absence of competition as no ligation of the Probe(Py) was observed in the presence of only Template(A) (lane 9).

Herein reactions involving the ligation of an unnatural pyrene:abasic base pair are described. Despite the lack of hydrogen bonding capabilities of this unnatural base pair, ligation of a 5'-phosphate pyrene-modified nucleotide showed great selectivity when positioned across from a model abasic lesion for two ligase enzymes, which was attributed to the stability and shape compatibility of the pyrene:abasic base pair. Moreover, the pyrene nucleotide was rapidly ligated with high conversion by both enzymes under conditions facilitating enhanced discrimination. These results indicate that selective ligation of pyrene nucleotide bearing probes can be applied to the sequence-specific detection of abasic lesions if ligation is coupled with a subsequent amplification of the ligated products to allow for detection of a small number of abasic sites. For example, single nucleotide polymorphisms (SNPs) have been detected in approaches involving first ligation templated by a target sequence followed by amplification of the ligated product. Such a strategy can be envisioned using ligation of a pyrene-terminated strand across from an abasic site. Other types of DNA adducts could also be detected in a sequence-specific manner using this approach by first converting them to abasic sites using the appropriate enzyme.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A method of ligating probes to form a ligation product for detecting abasic sites on a DNA target sequence comprising:

7 a) providing a pyrene probe;

b) providing a second probe;

c) providing a ligase;

d) providing said DNA target sequence;

e) ligating the pyrene probe to the second probe by templated ligation by hybridization with the DNA target sequence to produce said ligation product.

2. The method of claim 1, wherein the pyrene probe comprises a 5'-phosphate 1'-pyrene deoxyribonucleotide at the 5'-terminus.

3. The method of claim 2, wherein the second probe comprises a 3'-hydroxy probe having a terminal 3'-hydroxy that is ligated with the pyrene probe.

4. The method of claim 3, wherein the 5'-phosphate 1'-pyrene deoxyribonucleotide at the 5'-terminus of the pyrene probe is ligated with the 3'-hydroxy of the 3'-hydroxy probe.

5. The method of claim 4, wherein the ligase comprises T4 DNA Ligase.

6. The method of claim 4, wherein the ligase comprises PBCV-1 DNA Ligase.

7. The method of claim 4, wherein the abasic site is naturally occurring.

8. The method of claim 4, further comprising adding an enzyme to the DNA target sequence to produce an abasic site.

9. The method of claim 4, further comprising amplifying a sequence comprising at least a part of the ligation product.

10. The method of claim 4, further providing adenosine triphosphate (ATP), and further comprising adding said adenosine triphosphate (ATP) at a level of at least 1 millimolar.

11. The method of claim 10, further comprising adding the adenosine triphosphate (ATP) at a level of at least 5 millimolar.

12. The method of claim 10, further comprising adding the adenosine triphosphate (ATP) at a level of at least 10 millimolar.

13. The method of claim 10, further comprising adding the adenosine triphosphate (ATP) at a level of at least 15 millimolar.

14. The method of claim 1, wherein the ligase comprises T4 DNA Ligase.

15. The method of claim 14, further providing adenosine triphosphate (ATP), and further comprising adding said adenosine triphosphate (ATP) at a level of at least 10 millimolar.

16. The method of claim 1, wherein the ligase comprises PBCV-1 DNA Ligase.

17. The method of claim 1, wherein the abasic site is naturally occurring.

18. The method of claim 1, further comprising adding an enzyme to the DNA target sequence to produce an abasic site.

19. The method of claim 1, further comprising providing adenosine triphosphate (ATP)

at a level of at least 10 millimolar;

wherein the pyrene probe comprises a 5'-phosphate 1'-pyrene deoxyribonucleotide at the 5'-terminus, and wherein the second probe comprises a 3'-hydroxy probe having a terminal 3'-hydroxy; and wherein the 5'-phosphate of the pyrene probe is ligated with the 3'-hydroxy of the 3'-hydroxy probe; and wherein the ligase comprises T4 DNA ligase.

* * * * *